United States Patent [19]
Kluger et al.

[11] Patent Number: 5,917,020
[45] Date of Patent: Jun. 29, 1999

[54] BIS-TETRAMERIC HEMOGLOBIN AND REAGENTS FOR ITS PRODUCTION

[76] Inventors: Ronald H. Kluger, 14 Bradgate Rd., Don Mills, Ontario, Canada, M3B 1J7; Jodi J.L. Lock-O'Brien, 38 Winchester St. Apt. 1, Toronto, Ontario, Canada, M4X 1A7

[21] Appl. No.: 08/783,084

[22] Filed: Jan. 15, 1997

[51] Int. Cl.$^6$ .............. C07C 103/52; C07K 13/00; A61K 35/14
[52] U.S. Cl. .............. 530/385; 530/402; 530/410; 514/6
[58] Field of Search .............. 530/385, 402, 530/410; 514/6

[56] References Cited

U.S. PATENT DOCUMENTS

| | | |
|---|---|---|
| 4,857,636 | 8/1989 | Hsia . |
| 5,250,665 | 10/1993 | Kluger et al. . |
| 5,399,671 | 3/1995 | Kluger et al. . |
| 5,532,352 | 7/1996 | Pliura et al. . |

FOREIGN PATENT DOCUMENTS

| | | |
|---|---|---|
| WO97/00236 | 1/1997 | European Pat. Off. . |
| 94/11399 | 5/1994 | WIPO .............. C07K 13/00 |

OTHER PUBLICATIONS

K. Paal, R.T. Jones, & R.H. Kluger, J. Am. Chem. Soc. 118, 10380–10383.

He Huang, et al., "Multilinking Reactions Between Hemoglobin Tetramers in Solution and the Crystal", Artificial Cells, Blood Substitutes and Immobilization Biotechnology, vol. 22, No. 5, 1994, p. 106.

Zheng, Y., and Olsen, K.W., "Multilinking of Hemoglobin for Potential Blood Substitutes and Bioconjugates" (Meeting Abstract) Biophysicial Journal 1996, 70(2) Part 2, WP 390.

K. Paal et al.: A Site–Specific Tetrafunctional Reagent for Protein Modification: Cross–linked Hemoglobin With Two Sites for Further Reaction, Journal of the American Chemical Society, vol. 118, 1996.

Aharoni et al. Macromolecules 23(9): 2533–2549, 1990.
Aharoni et al. Macromolecules 22(8): 3361–3374, 1989.
Kluger et al. J. Am. Chem. Soc. 118(43): 10380–10383; Kluger et al. (1996a).
Kluger et al. J. Am. Chem. Soc. 118(37): 8782–8786; Kluger et al. (1996b).
Kluger et al. J. Am. Chem. Soc. 114(24): 9275–9280, 1992.
Delaney et al. Archives of Biochemistry and Biophysics 228(2): 627–638, 1984.

*Primary Examiner*—Michael P. Woodward
*Assistant Examiner*—Jay F. Williams
*Attorney, Agent, or Firm*—Ridout & Maybee; Robert G. Hirons

[57] ABSTRACT

Crosslinking reagents for protein modification are provided, which comprise four functional, leaving groups capable of reacting with amino acid residues on the protein chains, one pair at each end of a relatively rigid chemical spacer group comprising aromatic residues joined by amide linkages. Such crosslinking reagents react with hemoglobin to effect intramolecular crosslinking of two dimeric hemoglobin units to stabilize the tetramers, by use of the respective pairs of functional groups, and to produce dimers of such tetrameric units, i.e. bis-tetrameric, intramolecularly crosslinked and stabilized hemoglobin, to the exclusion of higher molecular weight hemoglobin species.

13 Claims, 3 Drawing Sheets

FIG. 1
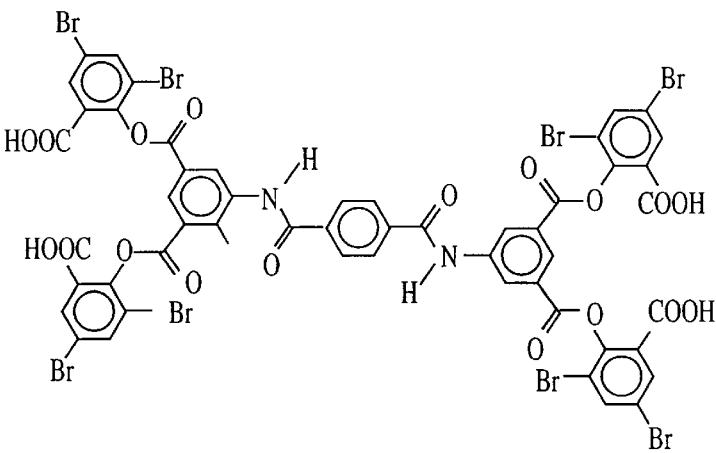
FIG. 2
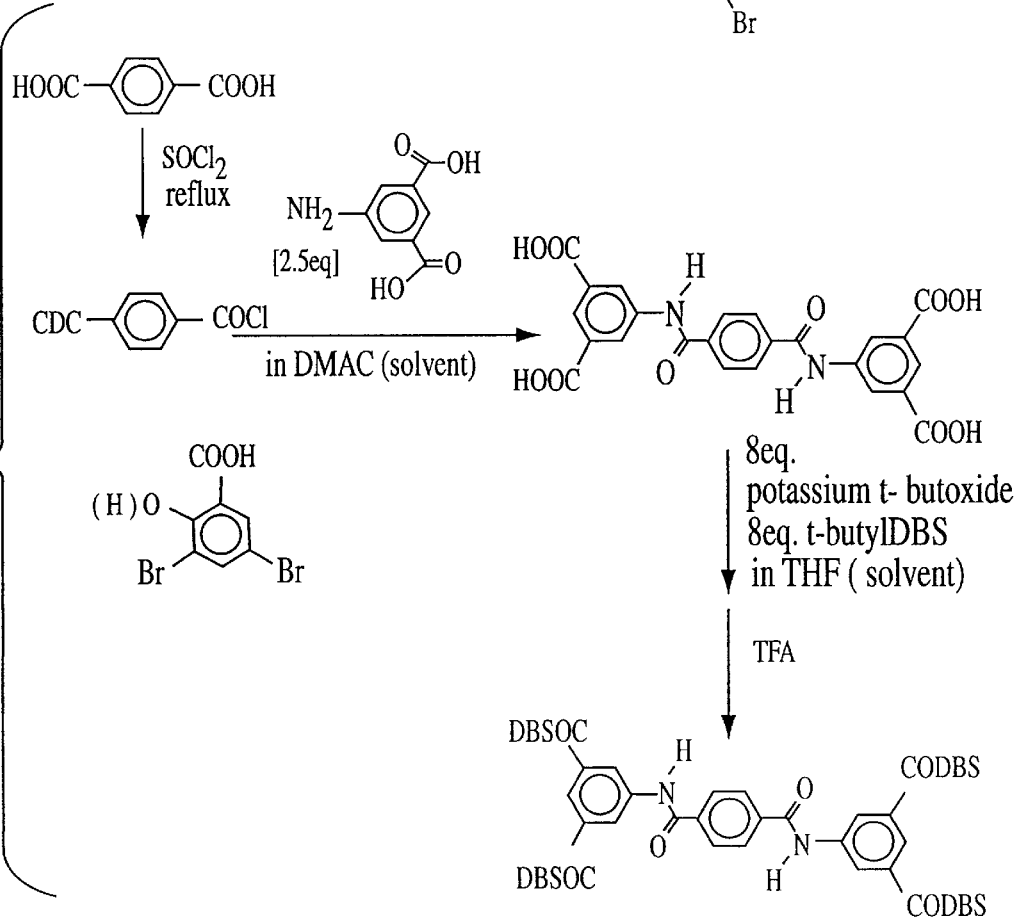
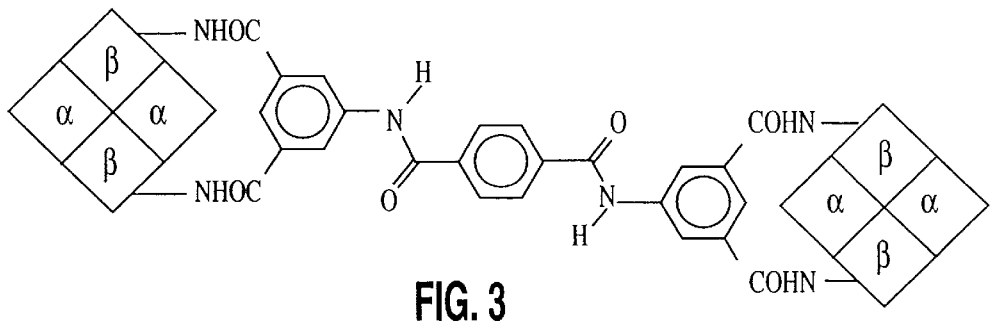
FIG. 3

BIS-TETRAMERIC HEMOGLOBIN AND REAGENTS FOR ITS PRODUCTION

FIELD OF THE INVENTION

This invention relates to crosslinking reagents for proteins such as hemoglobin, and more particularly to chemical crosslinking reagents having a plurality of reactive sites. From another aspect, the present invention relates to bis-tetrameric hemoglobin, i.e. hemoglobin in which the α, β sub-units are chemically crosslinked to form stable tetramers thereof, and the tetramers are also chemically coupled in pairs, to form bis-tetrameric hemoglobin of approximate molecular weight 128,000. The present invention also relates to processes for preparing bis-tetrameric hemoglobin using the chemical crosslinking reagents of the invention.

BACKGROUND OF THE INVENTION

Cross-linking reagents for the specific modification of human hemoglobin have been developed and reported previously. The cross-linked protein can potentially be used as a red cell substitute and also as a carrier in bioconjugation. Cross-linkers with structurally defined bridging moieties and highly selective reaction sites can produce specifically defined linkages in the protein. This permits altered properties of the modified protein to be clearly related to its structure.

Hemoglobin in the red blood cell consists essentially of four sub-units, two α-units and two β-units, each such unit including a heme molecule. Outside the red cell, this tetrameric hemoglobin tends to dissociate into αβ dimeric sub-units, and even further into monomeric sub-units. Such sub-units resulting from dissociation, of molecular weight c. 16,000 or 32,000, are too small for safe and effective use as a blood substitute in the mammalian system, since they tend to be excreted by the kidneys during circulation, and contribute to renal failure. Accordingly, it is usual to use hemoglobin, in a blood substitute, with chemical crosslinks formed between the selected subunits to bind the hemoglobin in its complete form, of molecular weight c.64,000, i.e. intramolecularly crosslinked hemoglobin. A variety of chemical crosslinking reagents have been proposed for this purpose.

A few of the crosslinking reagents previously proposed for intramolecular crosslinking of hemoglobin also cause incidental intermolecular crosslinking thereof, to form bis tetrameric hemoglobin of molecular weight c.128,000, tetrakis tetrameric hemoglobin of molecular weight c.256,000, and so on, up to species with molecular weight in excess of 1,000,000. These processes produce a mixture of such species, the reaction product thus having a wide molecular weight distribution. The optimum molecular weight, or molecular weight distribution, for hemoglobin for use as a blood substitute in mammals is still subject to study. Control over the molecular weight and molecular weight distribution is important, and this in turn means that control over processes of crosslinking hemoglobin, to yield a single species of crosslinked hemoglobin or a mixture containing known and controllable quantities of different species, is important.

REFERENCE TO THE PRIOR ART

U.S. Pat. No. 4,857.636 Hsia, issued Aug. 15, 1989 discloses intramolecular crosslinking and intramolecular crosslinking of hemoglobin with polyaldehydes obtained by oxidative ring opening of oligosaccharides, in a non-specific and generally uncontrolled manner, to obtain a product mixture comprising a variety of crosslinked hemoglobin species.

U.S. Pat. No. 5,532,352 Pliura et al, issued Jul. 2, 1996, describes a controlled process of crosslinking hemoglobin using the reagents proposed by Hsia, but under reaction conditions according to which control over the composition of the end product can be exercised.

U.S. Pat. No. 5,250,665 Kluger and Wodzinska, issued Oct. 5, 1993, discloses crosslinking hemoglobin with reagents such as trimesoyl tris(methyl phosphate) so as to react the crosslinking reagent with deoxy hemoglobin at the α-amino group of β-val 1 and the ε-amino group of lys 82 of both β-subunits, thereby effecting intramolecular crosslinking. This utilizes all of the functional groups of the crosslinking reagent in intramolecular crosslinking of the hemoglobin, thereby minimizing the formation of intermolecularly crosslinked hemoglobin species of molecular weight 128,000 and higher.

U.S. Pat. No. 5,399.671 Kluger and Song, issued Mar. 21, 1995, discloses that some reagents with three reaction sites can crosslink a protein such as hemoglobin with great efficiency and novel utility, but that once two sites on the trifunctional crosslinker have reacted, the third site may react with another group on the protein or remain available for reaction with exogenous reagents. The outcome depends on the functional group of the cross-linker. Reagents such as trimesoyl tris(3,5-dibromosalicylate) (TTDS) reacts only at β-lys 82 of the two β subunits, leaving the third ester group available reaction with added nucleophiles, and thereby providing a basis for bioconjugation and delivery of bioactive materials to the bloodstream of patients.

K. Paal, R. T. Jones and R. H. Kluger, *J. Am. Chem Soc.*, 118, 10380–10383, disclose a site-specific tetrafunctional reagent for protein-modification, especially hemoglobin modification.

SUMMARY OF THE INVENTION

It is an object of the present invention to provide novel crosslinking reagents for combining intra- and intermolecular crosslinking of proteins such as hemoglobin.

It is a further object to provide a process of crosslinking proteins such as hemoglobin that yields a crosslinked protein reaction product of controlled molecular weight distribution.

The present invention, from one aspect, presents multi-functional chemical reagents useful in crosslinking proteins such as hemoglobin, in a controlled manner. These reagents contain four functional groups capable of reacting with globin chains of hemoglobin to form covalent chemical links therewith, these functional groups being arranged in pairs. Each pair is separated from the other pair an appropriate distance, by a relatively rigid chemical spacer group. Each pair can react with either the a globin chains or the β globin chains, although normally the reaction is with the β chains. Individual members of each pair react with different β globin chains (or different a globin chains) of a sub-unit of a hemoglobin tetramer, to effect stabilization of the tetramer and to counteract the tendency towards dissociation into αβ dimers. In other words, the hemoglobin tetramer is intramolecularly crosslinked. Each pair of functional groups reacts to stabilize a different hemoglobin tetramer in this manner.

At the same time, since this is being effected by two pairs of functional groups on the same molecule, the tetramers stabilized by the respective pairs of functional groups are bonded together chemically by the crosslinking reagent, to form bis-tetrameric hemoglobin. The rigidity of the crosslinking reagent and the spacing between pairs of functional groups and individual members of a pair effectively prevents all functional groups from reacting with the same tetramer or with the same globin chain of a tetramer. Protein molecules in aqueous solution are separated from one another, due to electrostatic, and van der Waals, mutually repulsive forces. Accordingly, respective pairs of functional groups on the crosslinker are set to react with different protein molecules, not the same protein molecule, to produce the bis-tetramers of hemoglobin.

From another aspect, the present invention provides a process for preparing bis-tetrameric, intramolecularly crosslinked hemoglobin, which comprises reacting hemoglobin with a crosslinking reagent as defined above, under appropriate reaction conditions.

From a further aspect, the present invention provides bis-tetrameric, intramolecularly crosslinked hemoglobin, free from higher molecular weight hemoglobin species, and corresponding to the general chemical formula:

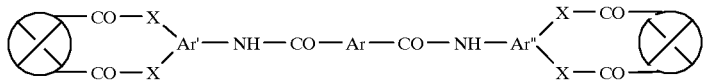

The crosslinking reagents of the present invention can be broadly defined as aromatic compounds corresponding to the general formula I:

(Z—Y—CO—X—)$_2$—Ar'—NH—CO—Ar—CO—NH—Ar"—(—X—CO—Y—Z)$_2$ in which: Ar, Ar' and Ar" represent aromatic moieties independently selected from phenyl, biphenyl, naphthyl and binaphthyl;

X represents a direct bond, an ethylene group or an —NH— group;

Y represents —O—, —S— or a direct bond;

and Z represents a chemical leaving group selected from lower alkyl phosphate, and phenyl substituted at the 2-position with a Bronsted base group such as carboxylate, and optionally substituted with up to 4 additional, independently selected substituent groups each of which is an electronegative group exhibiting a positive Hammett sigma value.

Bronsted base groups, as is well known, are proton acceptor groups. In addition to carboxylate, one can use phosphonate groups, sulfonate groups and the like.

Crosslinking reagents according to the invention thus comprise a chemical molecule having four chemical functional or leaving groups, arranged in pairs, each pair being disposed at an opposed end of a central chemical moiety of relatively rigid chemical structure, imparted by the amide linkages, and chemical length within a certain range.

Once the crosslinking reagents according to the present invention have effected the intramolecular crosslinking of two tetrameric hemoglobin units, and consequently have produced the bis-tetramer of hemoglobin, all reactive sites of the crosslinker have been used. There is no chemical residual reactivity on the crosslinker, and so there is no formation of higher molecular weight species of hemoglobin. Therefore, the 128 kD hemoglobin bis-tetramer product is produced, free from higher molecular weight species. The presence in the reaction product of lower molecular weight hemoglobin species, resulting from incomplete chemical reaction with the crosslinker, is possible, but these are easily removed by various size exclusion filtration techniques. Accordingly, the invention provides a means of obtaining bis-tetrameric hemoglobin, free from higher oligomeric hemoglobin species, by a single reaction step with the minimum of subsequent separation and fractionation steps, simply and economically. The resulting product can be used as is, as an oxygen carrier or blood substitute, or used for mixing and blending with other hemoglobin species of known composition to form a hemoglobin-based oxygen carrier or hemoglobin-based blood substitute.

in which

represents a hemoglobin tetramer, and X, Ar, Ar' and Ar" have the meanings given above.

BRIEF REFERENCE TO THE DRAWINGS

FIG. 1 is the structural formula of a first, specific, novel crosslinking reagent according to the invention, namely N,N'-5,5'-bis[bis(3,5-dibromosalicyl) isophthalyl] terephthalamide prepared according to Example 1 hereof, and hereinafter sometimes referred to as DBSIT;

FIG. 2 is a diagrammatic illustration of the process for synthesizing the product shown in FIG. 1, namely N,N'-5,5'-bis[bis(3,5-dibromosalicyl)isophthalyl] terephthalamide, according to the process of Example 1 hereof;

FIG. 3 is a diagrammatic illustration of the product produced according to Example 2 hereof;

DESCRIPTION OF THE PREFERRED EMBODIMENTS

Figure 4:
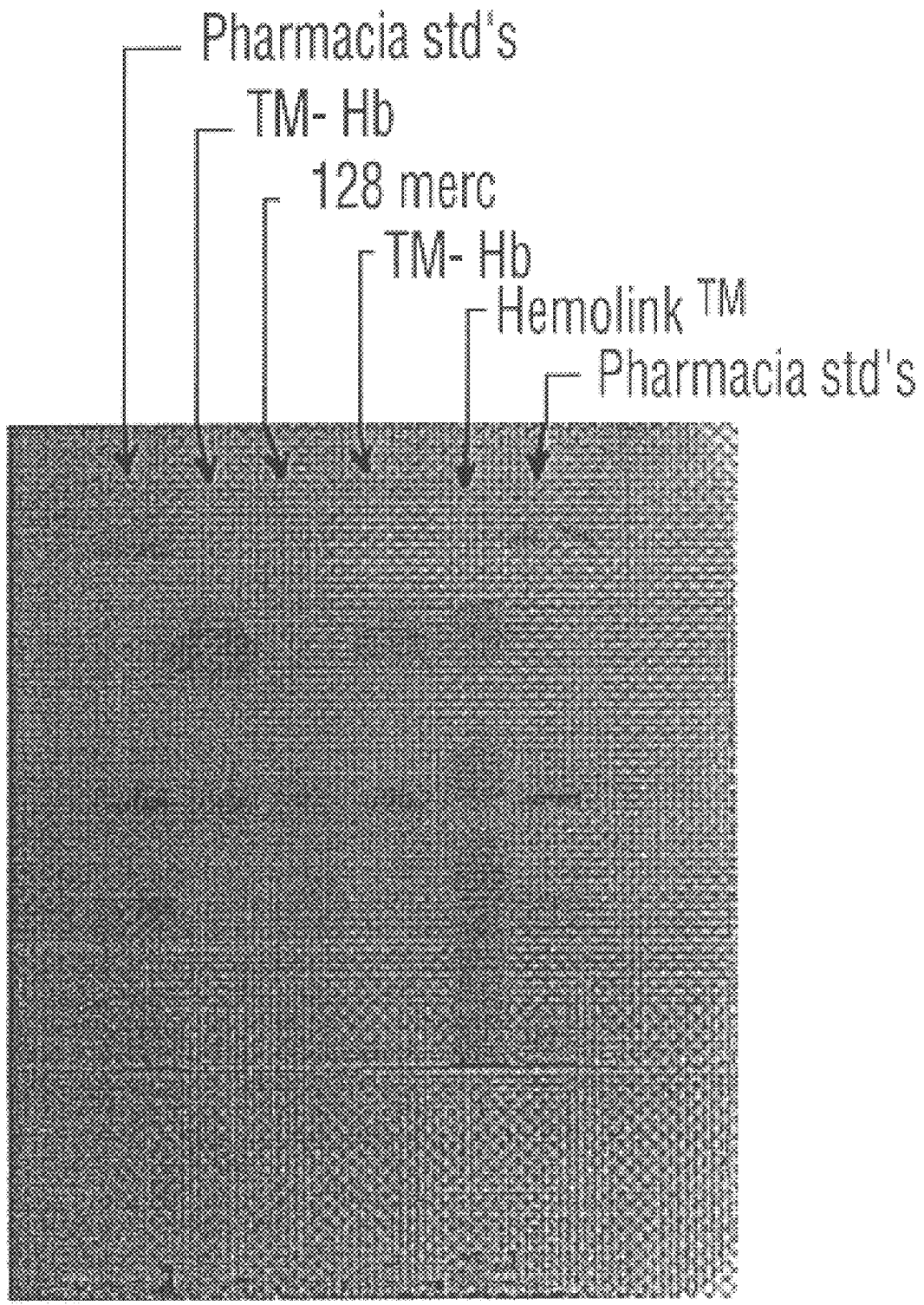
FIG. 4 is a diagrammatic presentation of the Native PAGE gel resulting from Example 4 below.

The protein with which the reagents of the present invention are reacted is preferably hemoglobin, especially human hemoglobin, and so the invention will be described hereinafter with specific reference to crosslinking of hemoglobin, although it is also applicable to other, similar proteins.

Preferred crosslinking reagents according to the invention are those in which Z represents substituted phenyl groups linked to the aromatic nucleus through ester linkages, i.e., wherein group Y in Formula I is —O—. Examples of suitable substituent groups with positive Hammett sigma values are acetamido (at the ortho or meta positions), acetoxy, acetyl, carbomethoxy, carboxy, halo, cyano, ethoxy (at the ortho or meta positions), hydroxy (at the ortho or meta positions), methanesulfonyl, methoxy (at the ortho or meta position), nitro, phenyl, trifluoromethyl and trimethylammonio. Preferred among such substituent groups are carboxyl, phosphonate, sulfonate, sulfate, phosphinate and halogen. Two or three such substituents are preferred, and especially cases where one of the substituents is carboxyl and another is halogen, especially bromo. When only one such substituent is present, it is preferred that it is located in the position ortho to the ester linkage to the phenyl group.

The particularly preferred crosslinking agents for use in the present invention are those which specifically crosslink hemoglobin, consistently and reproducibly, at specific, predetermined sites on the globin chains. In this way, one can reliably obtain a product with known, reproducible structure and properties each time the crosslinking agent is used, often a necessary precondition for the preparation of products to be used in biochemical applications.

One class of preferred crosslinking reagents according to the invention comprises 3,5-dibromosalicyl esters of tetracarboxylic acids. A specific such compound is N,N'-5,5'-bis[bis(3,5-dibromosalicyl)isophthalyl]terephthalamide, the structure of which is illustrated in FIG. 1 of the accompanying drawings. The present invention also provides a synthesis of this novel material and a process of reacting it with hemoglobin to produce bis-tetrameric, intramolecularly crosslinked hemoglobin.

In these compounds, the illustrated bromine substituents are readily replaceable, wholly or partially, and at other positions of the respective phenyl rings, with other electronegative groups selected from those referenced above for group Z, and which, at the position on the phenyl ring at which they are substituted, exhibit positive Hammett sigma values.

Suitable methods of preparing crosslinking reagents according to the present invention can be based on the readily available starting material terephthalic acid. After conversion to its acid chloride, this can be condensed with 5-amino isophthalic acid, in the presence of catalytic amounts of N,N-dimethylaminopropanol (DMAP) to obtain bis(3,5-dicarboxyphenyl)terephthalamide, a suitable intermediate from which a wide variety of crosslinking reagents according to the invention, in which Ar, Ar' and Ar" in the above formula are all phenyl, can be prepared. This is a modification of the method reported by Aharoni et al. (reference 1). Where alternative aromatic nuclei such as naphthyl, biphenyl and binaphthyl are chosen, appropriately modified starting materials and reagents are used, to give an intermediate compound with the required pair of amide linkages and functional groups ready for further reaction.

For preparation of the most preferred crosslinking reagent according to the present invention, DBSIT illustrated in accompanying FIG. 1, bis (3, 5-dicarboxyphenyl) terephthalamide can be reacted with t-butyl 3,5-dibromosalicylate according to the procedure of Klotz et al. (reference 2). This is generally illustrated in accompanying FIG. 2, and described in detail in specific Example 1 below.

The hemoglobin is preferably reacted with the crosslinking reagent in its deoxy form and under conditions which include the substantial absence of oxygen. The hemoglobin can, in the alternative, be reacted whilst in other protected forms such as carbon monoxylated Hb, but lower yields of crosslinked Hb are thereby obtained.

Reaction of hemoglobin with crosslinking reagents according to the preferred aspects of the present invention leads to both intramolecular crosslinking, in which covalent chemical bonds are formed between individual globin chains of subunits of the hemoglobin tetramer, and intermolecular crosslinking of tetrameric hemoglobin units to form bis-tetramers, of molecular weight c.128,000. Because of the designed chemical architecture of the crosslinking reagents, formation of hemoglobin species of higher molecular weight does not occur. There is no formation of compounds consisting of three, four, five, six or more covalently bound tetrameric hemoglobin units, because there are no more functional groups available on the crosslinking reagent for further reaction once the intramolecular crosslinks have been formed and two tetramers of hemoglobin have been linked by the crosslinking reagent. As is apparent from FIGS. 1 and 2 of the accompanying drawings, the DBSIT reagent has four functional, leaving groups, namely dibromosalicylate groups. The DBSIT molecules use all of their leaving groups in the chemical reaction with beta-globin chains of the hemoglobin to effect the intramolecular crosslinking to form stabilized tetramers. Moreover, two different hemoglobin tetramers will not link to the same pair of leaving groups of the crosslinking reagent, because of steric constraints.

In the reaction of the crosslinking reagent with the hemoglobin, it is preferred to use approximately stoichiometric quantities of the two reagents. If the crosslinking reagent is used in excess, there is a risk of undesirable hemoglobin modification without coupling of the tetramers of hemoglobin to form bis-tetrameric hemoglobin. If the hemoglobin is in excess, it is likely that the reaction product will be unnecessarily contaminated with unreacted hemoglobin. It is preferred to add the predetermined amount of solid crosslinking reagent slowly and gradually to the hemoglobin solution, by an infusion process, whereby the crosslinking reagent slowly dissolves in the hemoglobin aqueous solution, e.g. at pH about 8 using borate buffer, and reacts with the hemoglobin as it dissolves. This process counteracts the tendency of the leaving groups such as dibromosalicylate to hydrolyse off the crosslinker before the crosslinking reaction is complete. These leaving groups are generally reactive towards nucleophiles, designed to react with lysine groups, and hence having a tendency to hydrolyse in aqueous solution. An infusion or drip feed of the crosslinking reagent to the hemoglobin solution, so that hemoglobin is always in excess, counteracts this tendency.

In practice of the process of reacting hemoglobin with crosslinkers according to the present invention, the only significant protein byproduct which is found in the reaction mixture is one in which one of the covalent links to a β-globin chain has failed to form. This results in a product from which one α-β dimer can dissociate from one hemoglobin tetramer, leaving a product of about 96 kD, along with a 32 kD dimer. Such products, of significantly lower molecular weight, can be readily separated by routine size exclusion processes, if they are in fact formed to any significant extent.

The invention is further described and illustrated in the following specific examples. All NMR spectra were recorded on a Varian Gemini (200 MHz) spectrometer.

EXAMPLE 1

Sythensis of N,N'-5,5'-bis[bis(3,5-dibromosalicyl) isophthalyl]terephthalamide (DBSIT)

Materials and Methods

Commercial reagents were utilized without further purification. Solvents were dried prior to used. The purity of newly synthesized material was assessed by NMR spectroscopy, high pressure liquid chromatography and mass spectrometry.

Spectra

Proton and carbon NMR spectra were recorded on a Varian Gemini 200 MHz or 400 MHz spectrometer.

Biochemical Material

Reagents for the preparation of buffers and developers for the modifications of hemoglobin and for chromatography were all of analytical grade or better. Purified Hemoglobin A was provided by Hemosol Inc., Electrophoretic analysis was performed using polyacrylamide (12%) ready gels, and SDS-PAGE molecular weight standards (broad range).

Bis(3,5-dicarboxyphenyl)terephthalamide (4.1 mmol) was stirred and heated to reflux in thionyl chloride (10 mL) for 20 hours under nitrogen. The solvent was removed in vacuo, the resulting solid stirred in anhydrous tetrahydrofuran (20 mL) and then added slowly to a solution of t-butyl 3,5-dibromosalicylate (16.5 mmol) and potassium t-butoxide (16.6 mmol) in anhydrous tetrahydrofuran (60 mL). The resulting mixture was left to stir at room temperature for 20 hours under nitrogen. Ether (50 mL) was added, the mixture washed with distilled water (3.4 mL), the ether layer collected, dried with magnesium sulfate and the solvent removed in vacuo to give a yellow liquid. This product was stirred in trifluoroacetic acid (50 mL) at room temperature for 2 hours under nitrogen. Ether was added to precipitate additional product and the mixture left to stir at room temperature for 1 hour under nitrogen. The solution was then filtered to give a white solid in an unoptimized yield of 26%, m.p. 228–231° C. $^1$H NMR (ppm, DMSO-$d_6$): δ 11.0(s, 2H, N-H), 9.07(d, 4H, J=1.4Hz, ArH), 8.52(d, 2H, J=1.4 Hz, ArH), 8.38(d, 4H, J=2.40, ArH), 8.21(s, 4H, ArH), 8.12(d, rH, J=2.32 ArH). $^{13}$C NMR (ppm, DMSO-$d_6$): δ 165.2, 163.3, 162.3, 146.4, 140.6, 138.9, 136.9, 133.4 129.4, 127.9, 127.5, 126.1, 119.4, 119.2 MS (positive FAB): 1604 (found), 1604 (calculated).

This analysis is consistent with the structure of N,N'-5,5'-bis[bis(3,5-dibromosalicyl)isophthalyl]terephthalamide, (DBSIT), illustrated in accompany FIG. 1.

EXAMPLE 2
Reaction of DBSIT With Hemoglobin

Hemoglobin was reacted with DBSIT under various pH conditions (8.0 and 9.0), ligation states (carbonmonoxy and deoxy) and with different stoichiometric ratios of DBSIT:hemoglobin tetramer (2:1, 6:1). To prepare the stock solution, the Hb for reaction was eluted through a sephadex G-25 column equilibrated in the required reaction buffer (pH 8, 50 mM sodium borate buffer; pH 9, 0.1M sodium borate buffer).

For carbonmonoxy crosslinking, the resulting solution was then placed under carbonmonoxide flow for five minutes at room temperature, sealed and allowed to equilibrate in a 37° C. water bath for fifteen minutes. The crosslinker was added as a solid and dissolved completely within ten minutes. The carbonmonoxy-hemoglobin reactions were sealed following addition of the crosslinker.

To prepare deoxy-hemoglobin, the solution was photoirradiated under a stream of humidified oxygen for two hours at 4° C. in a rotating flask. It was then placed under a stream of humidified nitrogen for two hours at 37° C. in a rotating flask. The crosslinker was added as a solid and dissolved completely within ten minutes. The reaction was kept rotating under constant flow of humidified nitrogen for the duration of the reaction.

Both deoxy- and carbonmonoxy-hemoglobin reactions were contained in 50 mL round-bottom flasks immersed in a 37° C. water bath. Crosslinking was monitored via HPLC analysis at two hours and the reaction was terminated at 20 hours. The solution of modified hemoglobin was passed through a Sephadex G-25 column equilibrated with 0.1M MOPS buffer (pH 7.2) and collected for storage in a glass vial.

EXAMPLE 3
Analysis and Purification of Modified Hemogolbin

The extent of modification was assessed using c4 reverse-phase HPLC, as previously described.

Carbonmonoxy-hemoglobin was found to react incompletely with two equivalents of DBSIT at both pH 8 and pH 9. Deoxyhemoglobin behaved similarly at pH 9. C4 reverse phase HPLC analysis indicated that, after 20 hours, between one-half and two-thirds of the β-chains remained unmodified. There is no indication of α-chain modification. Six equivalents of DBSIT was found to push the reactions to modify all β-chains, but does not increase the yield of the higher molecular weight products. Two equivalents of DBSIT reacts with deoxyhemoglobin at pH 8 to modify 95% of β-chains after 20 hours, without α-chain modification.

The purity and molecular weight of products was assessed by FPLC and SDS-PAGE. A gel-filtration FPLC column was used under both associative (isocratic, 25 mM Tris pH 7.4, 0.4 and 0.6 mL.min) and dissociative (isocratic, 0.5M $MgCl_2$, 25 mM Tris pH 7.4, 0.4 mL/min) conditions. Unmodified hemoglobin and a sample of pure β82—β82 crosslinked hemoglobin were used as standards. The high molecular weight product was purified by collection of the fastest eluting band and concentration by centrifugation.

Polyacrylamide gel electrophoresis, under SDS denaturing conditions, separates the individual α and β protein monomers according to molecular weight. If two chains are covalently linked, they will travel as a single higher molecular weight species. This technique was used to assess the yield, purity and molecular weight of the crosslinked products. Prior to electrophoresis, the protein samples (crosslinked hemoglobin, hemoglobin and molecular weight standards) were denatured in boiling water for 5 minutes in 0.5M Tris-HCl buffer, pH 6.8, which contained 0.05% bromophenol blue, 4% v/v 2-mercaptoethanol, 2% sodium dodecyl sulfate, 10% v/v glycerol. Approximately 5 µg of protein was applied to each lane of the gel. The gel was run at 200 mV for approximately 30 minutes. The yield and purity could be estimated by visual comparison of the resolved electrophoretic bands after staining. Unmodified hemoglobin and molecular weight standards (broad range: 200 kD to 6.5 kD) were used to establish the molecular weight of the resulting bands. The results were recorded on photographs or photocopies.

These gels show a product with molecular weight of approximately 64 kda. Under the denaturing gel conditions, such a molecular weight could only result from the crosslinking of 4 globin chains. Since the c4 HPLC analysis shows no alpha chain modification, the 4 globin chains must all be beta. Each hemoglobin tetramer can contribute only two beta chains, therefore two hemoglobins must be intra- and intermolecularly crosslinked to get the 64 kda product under dissociative conditions. This is consistent with formation of the bis tetrameric hemoglobin. Collection of the fastest eluting band from the FPLC gel-filtration column and subsequent SDS-PAGE analysis of the isolated product shows that the bands corresponding to the 4 crosslinked beta chains (~64 kda), and unmodified alpha (~16 kda) increase in intensity (see lane 7) relative to the crude reaction mixture (see lane 6), while all other bands are reduced or removed. This is consistent with purification of the bis tetrameric hemoglobin product from the reaction mixture containing lower molecular weight hemoglobin species.

EXAMPLE 4
Molecular Weight Analysis

A sample of purified product prepared according to the process of the invention was analyzed by two methods to determine molecular weight distribution and degree of globin chain crosslinking.

Size exclusion chromatography under dissociating conditions (SEC-DIS) involves passing a sample through a chromatographic medium with a constant, controlled flow of an eluting buffer containing 500 mM $MgCl_2$. The chromatographic medium consists of gel beads having variably sized pores. The proteins, if sufficiently small, may pass into the pores of the gel and be slowed in their progress through the column. Larger proteins will not pass into the pores and are not slowed in their progress. A mixture of proteins moving under the influence of the eluting buffer will thereby elute in order of decreasing molecular weight. The buffer used in this instance was of 500 mM $MgCl_2$+25 mM Tris, pH adjusted to 7.20. The high concentration of magnesium chloride was sufficient to dissociate any non-crosslinked Hemoglobin into two αβ dimers. The sample provided was diluted 1:1 with Milli-Q water followed by a 50 μL injection onto a Pharmacia Superdex™ 200 analytical column (10 mm×30 cm). Two replicate samples were run.

Size Exclusion Chromatography showed a single major peak eluting at approximately 34 min. representing 93% of the eluted protein. A shoulder on the high molecular weight side at 30.3 minutes represented roughly 4.7% and a high molecular weight moiety at 21 minutes represented approximately 2%. The major peak at 34 minutes eluted at the same as the 128 kDa fraction of a standard crosslinked hemoglobin (within experimental variability) non-crosslinked hemoglobin and are therefore an approximation of in vivo conditions.

Native PAGE separates proteins based largely on their molecular weight, although shape and charge can influence mobility. Samples were analyzed using Pharmacia's Phast Homogeneous Native Page 12.5 gel run on Pharmacia's Phast System Separation unit. The staining procedure was according to Pharmacia's guidelines for Phast Gel Native Page. The gel was scanned using Bio-Rad's GS-670 imaging densitometer. The following samples were applied to the gel:

| Lane | Sample | Molecular Weight Profile (kDa) |
| --- | --- | --- |
| 1 | Molecular weight standard mixture | 67, 140, 232, 440, 669 |
| 2 | TM-Hb | 64, 128 |
| 3 | 128mer | analyte |
| 4 | TM-Hb | 64, 128 |
| 5 | Hemolink ™ | 64, 128, >128 |
| 6 | Molecular weight standard mixture | 67, 140, 232, 440, 669 |

TM-Hb is an abbreviation for trimethylphosphate-crosslinked hemoglobin—see aforementioned U.S. Pat. No. 5,250,655 Kluger et al. Hemolink™ denotes O-raffinose-crosslinked hemoglobin—see aforementioned U.S. Pat. No. 5,532,352 Pliura et al. 128mer denotes the product of the present invention.

The image of the Native PAGE gel is diagrammatically presented in FIG. 4.

Figure 5:
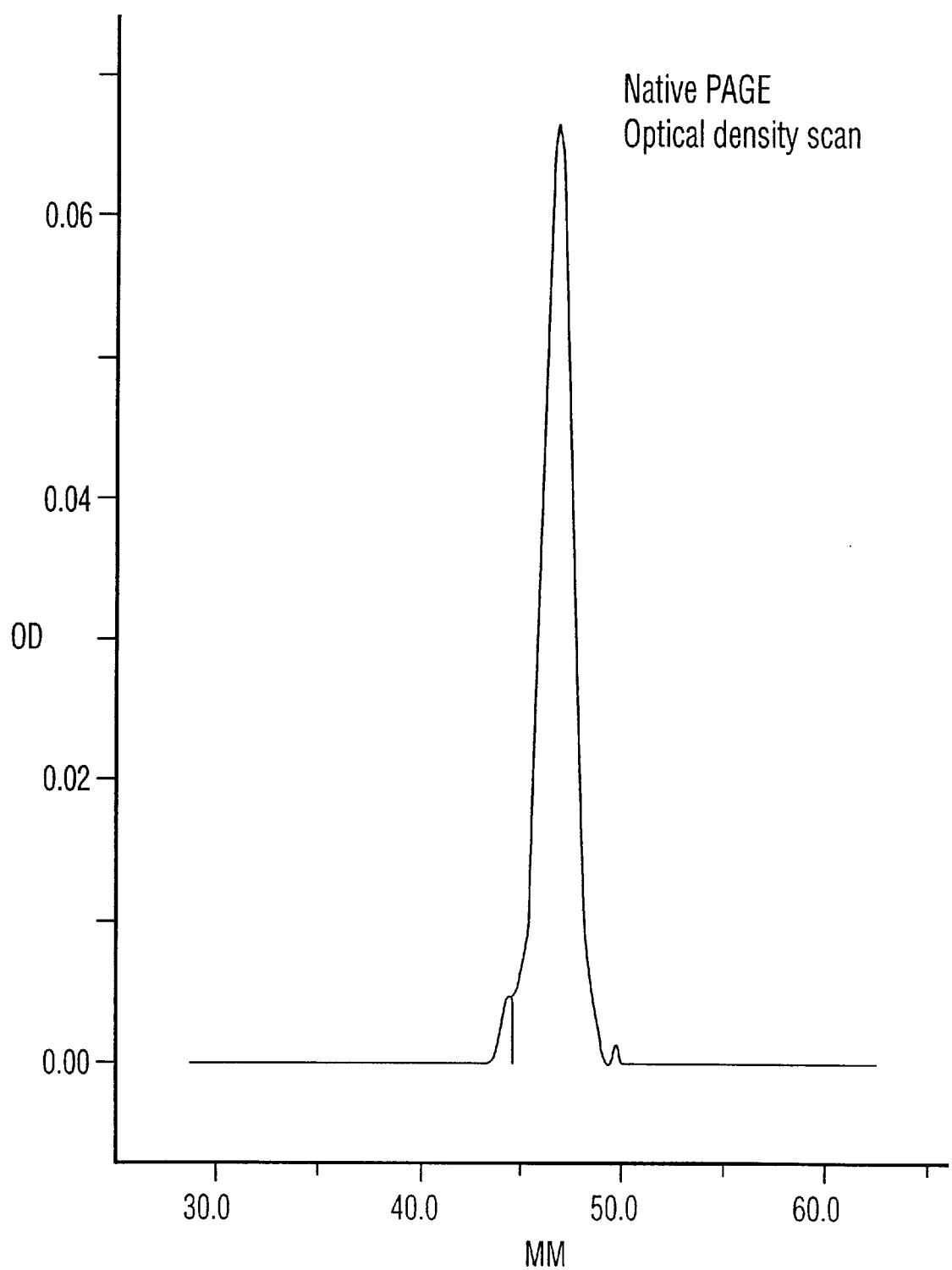
FIG. 5 is an optical density scan from the Native PAGE analysis described in Example 4 below.

Native PAGE shows a single band for the 128mer sample which aligns with a minor band of the TM-Hb sample and with the lactate dehydrogenase band of the standard mixture. The 128mer band also aligns closely with the 128mer band of Hemolink™. The optical density scan shows a single major peak in the 128mer prepared according to the invention, FIG. 5.

REFERENCES

1. Aharoni, F. M., et al. "Macromolecules", 1989: Vol. 22; pp 3361–3374.
2. Delaney, E. J., Klotz, et al., "Archives Biochem. Biophys.", 1984; 228, pp 627–638

What is claimed is:

1. A crosslinking reagent for intramolecularly crosslinking hemoglobin and for forming bis-tetramers thereof, said crosslinking reagent having to the general formula I:

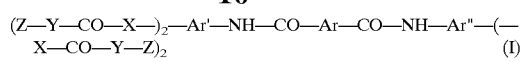

in which: Ar, Ar' and Ar" represent aromatic moieties independently selected from phenyl, biphenyl, naphthyl and binaphthyl;

X represents a direct bond, an ethylene group or an —NH— group;

Y represents —O—, —S— or a direct bond;

and Z represents a chemical leaving group selected from lower alkyl phosphate, and phenyl substituted at the 2-position with a Bronsted base group, and said phenyl also being optionally substituted with up to four additional independently selected substituent groups, each of which is an electronegative group exhibiting a positive Hammett sigma value.

2. The crosslinking reagent of claim 1 wherein Y in general formula I represents —O—.

3. The cross-linking agent of claim 2 wherein group Z is phenyl substituted at the 2-position with a Bronsted base group and optionally substituted with up to four additional electronegative groups independently selected from the group consisting of acetamido, acetoxy, acetyl, carbomethoxy, carboxy, halo, cyano, ethoxy, hydroxy, methanesulfonyl, methoxy, nitro, phenyl, phosphinate, trifluoromethyl, trimethylammonio, phosphate, sulfonate, sulfate, phosphonate, halogen and diphosphinate.

4. The cross-linking reagent of claim 3 wherein the Bronsted base group is carboxy.

5. The cross-linking reagent of claim 4 wherein the phenyl group Z has 2 or 3 electronegative group substituents.

6. The cross-linking reagent of claim 5 wherein the electronegative groups substituted on the phenyl of group Z in general formula I are selected from the group consisting of carboxy, phosphonate, sulfonate, sulfate, phosphinate and halogen.

7. The crosslinking reagent of claim 6 wherein the group Z in general formula I is 3,5-dibromosalicyl.

8. A process of preparing intramolecularly crosslinked bis-tetrameric hemoglobin which comprises reacting hemoglobin with a crosslinking reagent as defined in claim 1.

9. The process of claim 8 wherein the hemoglobin is human hemoglobin.

10. The process of claim 9 wherein the hemoglobin is reacted with the crosslinking reagent in its deoxy form and the reaction takes place in the substantial absence of oxygen.

11. The process of claim 8 wherein the cross-linking reagent is added gradually to an aqueous solution of the hemoglobin, until a stoichiometric amount of cross-linking reagent has been added.

12. Bis-tetrameric, intramolecularly cross-linked hemoglobin, free from higher molecular weight hemoglobin species.

13. Bis-tetrameric, intramolecularly cross-linked hemoglobin according to claim 12 and corresponding to the general Formula:

wherein X, AR, AR' and AR" have the meanings given in claim 1, and the circle designations represent tetrameric hemoglobin.

* * * * *